United States Patent
Kourtakis et al.

(10) Patent No.: US 6,921,831 B2
(45) Date of Patent: Jul. 26, 2005

(54) MODIFIED BIMO CATALYST AND PROCESS FOR USE THEREOF

(75) Inventors: Kostantinos Kourtakis, Media, PA (US); Patrick Mills, Newark, DE (US); Carl Z. Cao, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/342,608

(22) Filed: Jan. 15, 2003

(65) Prior Publication Data

US 2003/0162981 A1 Aug. 28, 2003

Related U.S. Application Data

(60) Provisional application No. 60/349,642, filed on Jan. 18, 2002.

(51) Int. Cl.[7] .................. C07D 305/00; C07C 5/09; B01J 27/152; B01J 27/057
(52) U.S. Cl. .................. 549/429; 549/505; 549/506; 585/622; 585/624; 585/631; 585/906; 502/212; 502/215; 502/311; 502/317
(58) Field of Search ................ 549/429, 505, 549/506; 502/212, 215, 311, 317; 585/622, 624, 631, 906

(56) References Cited

U.S. PATENT DOCUMENTS 3,894,055 A 7/1975 Farha, Jr.
3,894,056 A 7/1975 Bertus et al.
4,278,826 A 7/1981 Tremont et al.
4,309,355 A 1/1982 Parthasarathy et al.
4,322,358 A 3/1982 Bither, Jr. et al.
5,780,700 A 7/1998 Hagemeyer et al.

FOREIGN PATENT DOCUMENTS

DE   197 05 325   8/1988
DE   197 05 328   8/1998

OTHER PUBLICATIONS

"Oxidation of Butadiene to Furan", Semanov Institute of Chemical Physics, Moscow, Russia, Dec. 1, 1999.

"Gas Phase Catalytic Oxidation of Butadiene to Furan", Semanov Institute of Chemical Physics, Moscow, Russia, Mar. 1, 2000.

"Gas Phase Catalytic Oxidation of Butadiene to Furan", Semanov Institute of Chemical Physics, Moscow, Russia, Jun. 1, 2000.

"Oxidation of Butadiene to Furan", Semanov Institute of Chemical Physics, Moscow, Russia, Sep. 1, 2000.

*Primary Examiner*—Cecilia J. Tsang
*Assistant Examiner*—Raymond Covington

(57) ABSTRACT

Modified lead/bismuth/molybdate catalysts containing vanadium, copper, or gold have been prepared, and are selective to the corresponding furan compound from the gas phase oxidation of an unsaturated acyclic hydrocarbon such as butadiene.

34 Claims, No Drawings

MODIFIED BIMO CATALYST AND PROCESS FOR USE THEREOF

This application claims the benefit of U.S. Provisional Application No. 60/349,642, filed Jan. 18, 2002.

FIELD OF INVENTION

This invention concerns a catalyst and process useful in the oxidation of hydrocarbons. The catalyst may contain molybdenum, bismuth, lead and oxygen, modified with copper, vanadium or gold.

BACKGROUND

Furan is an important intermediate for the production of many commercial products. In particular, furan can be easily hydrogenated to tetrahydrofuran, which is used in many industrial polymers.

Molybdenum-based catalysts have been widely used for the production of furan from butadiene. Vanadium, phosphorus and bismuth are known for use as co-catalysts or promoters. Catalysts that have been used previously include bismuth molybdates modifiable with sodium, silver or calcium and/or other metals (U.S. Pat. No. 4,322,358); silver molybdates modifiable with bismuth (U.S. Pat. No. 4,309,355); and molybendum/cobalt/phosphorus/oxygen compounds (U.S. Pat. No. 3,894,056).

Bismuth oxides modifiable with several elements including molybdenum have been used for the oxidative dehydrogenation of alkylaromatics and paraffins to produce olefinic unsaturated compounds (U.S. Pat. No. 5,780,700).

A need remains, however, for a catalyst that has a high selectivity to furan compounds in the oxidative dehydrogenation of unsaturated acyclic hydrocarbons, thereby obtaining increased yields of the desired furan compound as the reaction product.

SUMMARY OF THE INVENTION

In one aspect, this invention is a mixed metal oxide catalyst containing (a) bismuth, lead, molybdenum and oxygen, and (b) at least one metal selected from the group consisting of copper, gold and vanadium.

In another aspect, this invention is a process for the oxidation of an unsaturated acyclic hydrocarbon having 4–10 carbon atoms, such as an alkene or alkadiene, to the corresponding furan compound in an oxygen-containing environment using a catalyst as described above.

It has unexpectedly been found that the catalyst of this invention, as described herein, or the use of such a catalyst in the process of this invention, as described herein, increases the selectivity to furan compounds in the oxidative dehydrogenation of unsaturated acyclic hydrocarbons, thereby obtaining increased yields of the desired furan compound as the reaction product.

DETAILED DESCRIPTION OF THE INVENTION

The catalyst of the present invention is used in the production of furan compounds by the oxidation of 4–10 carbon unsaturated acyclic hydrocarbons, such as alkenes and alkadienes. Preferred is the vapor phase oxidation of butene or butadiene to furan. The catalyst contains molybdenum, bismuth, oxygen and lead, and at least one element selected from the group consisting of copper, vanadium, and gold. This catalyst is more selective to furan in the oxidation of alkenes and alkadienes, and/or results in higher yields (conversions).

In one embodiment, the catalyst may contain molybdenum, bismuth, oxygen and lead, and at least one element selected from the group consisting of copper, vanadium, and gold. The elements should be present in the catalyst in amounts sufficient to provide increased selectivity and conversion to furan type compounds from alkenes and alkadienes as compared to a catalyst not containing the same elements. In another embodiment, the catalyst may be a compound of the formula $Q_d[Bi_aPb_bMo_cO_y]_eO_x$ wherein Q is selected from the group consisting of copper, gold and vanadium, or mixtures thereof; a is about 1 to about 3; b is about 0.01 to about 0.1; c is about 0.1 to about 2; d is about 0.01 to about 2; e is about 0.01 to about 2; and y and x are independently numbers sufficient so that the oxygen present balances the charges of the other elements in the compound. X in certain embodiments may be 0. The value of d is not affected by the selection of two or more of copper, gold and vanadium as Q. More preferably a is about 1.5 to about 2.0; b is about 0.025 to about 0.075; c is about 0.5 to about 1.5; d is about 0.05 to about 1; and e is about 0.5 to about 1. Most preferably the catalyst contains copper; a is about 1.95; b is about 0.05; c is 1; and d is about 0.029 to about 0.5. In different embodiments, the catalyst may consist of, consist essentially of or comprise the elements named above.

The oxidation is performed in an oxygen-containing environment. The oxygen in the oxygen-containing environment may be provided by an external feed of an oxygen containing gas, which can be molecular oxygen; oxygen mixed with inert gases such as nitrogen or helium; or air. When an external feed stream is used, the amount of oxygen in the feed stream may be 10–25 mole %, with about 10–20 mole % being preferred. Alternatively, however, the oxygen in the oxygen-containing environment is provided solely by the oxygen contained in the catalyst.

The catalyst of this invention is believed to provide increased oxygen capacity in the catalyst's crystal lattice, i.e. the mobile or "reactive" oxygen contained in the catalyst. In the case of the oxidation of butadiene, for example, the catalyst is believed to be selective to furan and/or to provide increased selectivity towards furan by the oxidation of butadiene in the absence of gas phase oxygen. Increases in selectivity towards furan by, for instance, an increase in the selective "reactive" oxygen in the crystalline lattice ultimately leads to overall improvements in the yields of furan from the butadiene oxidation process. While the present invention is not bound by any theory, it is believed that the increased oxygen capacity of the catalyst of this invention, selective to furan, allows this catalyst to effectively catalyze high conversion to furan, even under conditions where the catalyst is the only source of oxygen for butadiene. Use of the catalyst of this invention, consequently, provides advantages in safety of operation as well as conversion, because one can operate at levels of oxygen in the feed which are well outside the explosive range of conventionally-used hydrocarbon/oxygen/inert gas mixtures, for example those known for use when oxidizing butadiene.

The catalyst of this invention can be either a particular structure, containing a desired ratio of cations, or a combination of structures that together contain the desired ratio of cations. The catalyst may thus be a mixture of the crystalline oxides of the compound of the formula given above, and may further include the amorphous phase of the compound. Another distinguishig feature of the catalyst of this invention is that the active ingredient in the catalyst, typically a metal oxide or a mixture of metal oxides, will operate according to the two-step process described by Mars and Van Krevelen in *Chemical Engineering Science* (Special Supplement) Vol.3, 1954, page 41.

The catalyst can be prepared by any method that results in a composition with the desired combination of elements, including coprecipitation, impregnation, sol-gel techniques, aqueous or nonaqueous solution or suspension mixing, freeze drying, spray roasting, spray drying or dry mixing. Ceramic methods, i.e., solid state techniques could be used, but are, in general, less preferred. Certain of the compounds are better prepared by one method rather than another as appreciated by one of ordinary skill in the art. Small or trace amounts of elements other than the desired elements may be present in the final composition.

A process for the preparation of the catalyst involves contacting at least one cation-containing compound with at least one other cation-containing compound for each of the other cations of the final catalyst compound in a solution containing water to form a resultant solution or colloid, evaporating the solution to dryness, and heating the resultant material to form the catalytic compound.

A preferred method of preparation involves preparation of a crystalline bismuth lead molybdate prepared by refluxing the appropriate precursors (such as bismuth oxynitrate, lead nitrate or ammonium molybdate). Cu, V or Au can be added as soluble precursors which are contacted with the preformed bismuth lead molybdate. This material can then be heated in air at a higher temperature to form the final catalyst. Variations of this technique, such as coprecitating the bismuth lead molybdate with Cu, V Au precursors during the reflux process are also possible.

The catalyst is prepared at normal atmospheric pressure, but elevated or reduced pressures can be employed. Agitation is not required, but is usually provided to facilitate a homogeneous mix and to facilitate heat transfer.

The catalyst may optionally be supported on conventional catalytic solid supports including but not limited to alumina, titania, silica, zirconia, zeolites, clays, or mixtures thereof. Preferred supports are aluminum oxide, particularly alpha $Al_2O_3$, and titanium oxide. Any method known in the art to prepare the supported catalyst can be used.

The catalyst in the present invention can be dried using any known method, including freeze drying, spray drying, and spray roasting.

Freeze drying procedures can accommodate several catalyst compositions, and are useful if the catalyst precursors are soluble in water or other solvent which can be rapidly frozen. Precursor salts are dissolved in an appropriate amount of solvent to form a solution or fine colloid. The solution is then rapidly cooled and frozen by immersion in a suitable medium, such as liquid nitrogen. If the solution is rapidly frozen, the salts and other components will remain intimately mixed and will not segregate to any significant degree. The frozen solid is transferred to a freeze drying chamber. The solution is kept frozen while water vapor is removed by evacuation. Refrigerated shelves are used to prevent thaw-out of the frozen solids during evacuation.

Freeze drying procedures for catalyst compositions in the present invention involve the use of soluble precursor salts. Solution concentrations can vary widely, and can range from 0.1 M to 10 M, depending on the solubility of the precursor salts used. Solutions are preferably rapidly frozen (<<1 min) to preserve intimate mixing of the precursor salt components. Evacuation times can vary from day(s) to week(s), depending on the quantity of solvent to be removed. Catalyst materials are typically calcined, either ex situ or in situ to produce the final, active form. Catalyst precursor solutions can also be soaked, added or impregnated into porous catalyst monoliths, frozen, dried and calcined as described above. In some cases, the catalyst precursors of gold, vanadium and copper can be soaked, added or impregnated into a preformed bismuth lead molybdate powder, frozen, dried and then calcined as described above.

Spray drying procedures involve the use of solutions, colloids or slurries containing catalyst precursors or catalyst compounds. The technique consists of atomization of these liquids (usually but not exclusively aqueous) into a spray, and contact between spray and drying medium (usually hot air) resulting in moisture evaporation. The drying of the spray proceeds until the desired moisture content in the dried particles is obtained, and the product is recovered by suitable separation techniques (usually cyclone separation). A detailed description of spray drying methods can be found in "Spray Drying Handbook", 4th edition by K. Masters (Longman Scientific and Technical, John Wiley and Sons, N.Y.) c. 1985.

Spray roasting also involves the use of solutions or colloids, but generally involves drying and calcination (at higher temperatures) in one process step to produce catalyst powders.

The catalyst of the present invention can also be prepared by a sol gel process. In this case, the gold, vanadium or copper bismuth lead molybdate may be incorporated in a sol gel "matrix" derived from a number of alkoxides. For instance, one or more metal alkoxides (e.g., tetraethylorthosilicate) may be used as starting material for preparing the gels. The inorganic metal alkoxides used to prepare the catalyst may include any alkoxide which contains from 1 to 20 carbon atoms, preferably 1 to 5 carbon atoms, in the alkoxide group. It is preferred that these alkoxides are soluble in the liquid reaction medium. $C_1$–$C_4$ alkoxides are most preferred. An example of a most preferred $C_1$–$C_4$ alkoxide is aluminum isopropoxide.

An aqueous solution containing at least one dissolved metal salt (containing bismuth, lead, molybdenum precursors with gold, copper, or vanadium) is added to a non-aqueous solution of at least one alkoxide, typically selected from the group consisting of magnesium, silicon, and aluminum alkoxides to induce a hydrolysis and condensation reaction of the alkoxides to form a gel. The solution is prepared in a moisture-free environment, preferably under inert conditions, for example a nitrogen blanket. It is also preferable that the hydrolysis reactions that induce gel formation be performed under a moisture-free, inert-gas environment so that the hydrolysis can be controlled during the contacting step of the non-aqueous with the aqueous solutions. The material can be conventionally or supercritically dried to produce a xerogel or aerogel.

The catalyst material of the present invention can also be prepared as attrition resistant microspheres, useful in fluidized bed, recirculating solids, or moving bed reactors. Such processing, which typically involves spray drying the catalyst particles with a suitable binder to form microspherical particles which are attrition resistant, and have the appropriate size ranges, are described in U.S. Pat. No. 4,769,477 and U.S. Pat. No. 5,543,532.

For instance, an abrasion resistant coating of silica can be used to make these spheroidal particles (or microspheres) attrition resistant. A silica coating can be formed by (a) forming a slurry comprised of catalyst or catalyst precursor particles dispersed in an aqueous silicic acid solution equivalent to a weight of $SiO_2$ not exceeding about 6% by weight, the relative amounts of the particles and silicic acid chosen so that the weight of the $SiO_2$ formed is about 3–15% of the total weight of the particles and the $SiO_2$, (b) spray drying the slurry to form porous microspheres of attrition resistant catalyst or catalyst precursor, and (c) calcining the spray dried microspheres at an elevated temperature which is below the temperature which is substantially deleterious to the catalyst, to produce attrition resistant $SiO_2$ coated catalyst.

In this case, preferably, the silicic acid is polysilicic acid having an equivalent concentration of $SiO_2$ not exceeding about 5% by weight; the catalyst or catalyst precursor particles are less than about 10 μm in diameter; the microporous spheroidal particles produced by spray drying have diameters of from about 10 μm to about 300 μm; and the relative amounts of particles to be spray dried and $SiO_2$ are chosen so that the weight of the $SiO_2$ is about 5–12% of the total weight of the particles and the $SiO_2$. It is preferred that the size of the particles used in step (a) above are from about 0.5 μm to about 10 μm and most preferably from about 0.5 μm to about 3 μm. This material can be used in fluid bed or recirculating solid reactor configurations.

For fixed bed microreactor evaluations, prior to use, the catalyst of this invention is typically formed into a convenient catalyst shape by pelletizing the catalyst at about 30,000 psi ($2.07 \times 10^6$ kPa) or less, to form small disks and crushing the pellet through sieves. For fixed bed reactor evaluations, typically a −40/+60 mesh sieve is used (U.S. Sieve Series), which is a sieve that will pass a particle of mesh size 40 or less but that will not pass a particle of mesh size 60 or more. Optionally, one could blend the resultant powder with 1–3% of a die lubricant and pellet binder, such as graphite or Sterotex®, a hydrogenated cottonseed oil, commercially available from Capital City Products Company, Columbus, Ohio, before tabletting. For fluidized bed reactor use, the preferred size range is 20 to 150 micrometers.

Although the catalyst of this invention may be used in a pulse reactor, a steady state fixed bed reactor, a recirculating solids reactor, or a fluid bed reactor, it is to be understood that the process of this invention is not limited to any particular type of reactor. The process can be performed in any suitable reactor such as but limited to a pulse, fluidized bed, fixed bed, steady state riser reactor, and a recirculating solids reactor system. The term "recirculating solids reactor system" is used to mean a general reaction system with two reaction zones, in which two separate reactions take place, and which uses as the catalyst a particulate solid which circulates between the two reaction zones and takes part in both reactions.

Optionally, either or both reaction zones may take place in a transport bed reactor or a fluidized bed reactor. The term "transport bed reactor" is used to mean any reactor in which catalyst particles are injected at one end of the reactor and carried along with gas reactants at high velocities and discharged at the other end of the reactor to a gas-solids separation vessel, whereas in a fluidized bed reactor the catalyst typically recirculates within the reactor for an extended period of time. A riser reactor, in which the reactor is a vertical pipe wherein the catalyst and gases are fed in at the bottom, transported in essentially plug flow and removed at the top, is one example of a transport bed reactor. Another example is a pipeline reactor, in which the flow of catalyst and gases is other than vertically upwards. A transport bed reactor, as defined herein, includes a riser reactor or pipeline reactor which also incorporates a zone for fast fluidization, i.e., a zone where the gas velocities are sufficiently high to carry out a substantial portion of the catalyst fed, but with more back-mixing of catalyst than would occur in plug flow.

A two-step process permits independent control of the reactant gas concentrations, the gas residence time, and the catalyst residence time in each zone for optimum operation, and enables several advantages of the above reactive concept over the single-step fixed bed or fluidized bed alternative. High selectivity is achieved because of plug flow and optimum oxidative state of the catalyst. Significant reductions are realized in product recovery costs because the regeneration off-gas stream is kept separate from the product gas stream, resulting in a highly concentrated product stream. High throughput rates are attributed to the independent control of variables for the two steps of the operation, resulting in reduced investment and decreased catalyst inventory. Conventionally, an abrasion resistant coating of silica is used to make these spheroidal particles (or microspheres) attrition resistant.

A riser or transport line reactor is characterized by high gas velocities of from about 5 ft/s (about 1.5 m/s) to greater than 40 ft/s (12 m/s). Typically, the reactor line is vertically mounted with gas and solids flowing upward in essentially plug flow. The flow can also be downward, and the reactor line can be mounted other than vertically. With upward flow of gas and solids, there can be a significant amount of local back mixing of solids, especially at the lower end of the velocity range. A fluidized bed reactor is characterized by extensive solids back mixing.

The process of this invention is run under suitable vapor-phase reaction conditions for the conversion of a 4–10 carbon unsaturated acyclic hydrocarbon, such as an alkene or alkadiene, to the corresponding furan compound. Reaction temperatures can vary from about 350° C. to about 600° C., with the preferred temperature range being about 350° C. to about 550° C., depending upon the catalyst activity. Reactor pressure can vary from atmospheric to superatmospheric, with 1–3 atmospheres (about 100-300 kPa) being preferred. Nominal contact times, that is, the time that the feed stream is in contact with the catalyst, as expressed by the ratio of bulk catalyst volume to gaseous feed volume passed over the catalyst per second (gas flows calculated at room temperature) can vary from about 0.1 to 10 seconds, with about 0.25–1 second being preferred.

If the catalyst compositions described herein lose activity during use through partial reduction or through carbonization, they can be regenerated, if desired, by refiring in air at substantially the same temperature as that used in the initial calcination step. Calcination temperatures for these catalysts can vary from about 200° C. to about 800° C., with the preferred temperature range being about 350° C. to about 600° C. Calcination times can vary from 1 to 36 hours with the preferred time being about 6–18 hours. Furan can be isolated from the products of the reactions by any appropriate means. The effluent from the reactor can also be recycled and reacted further.

The furan-type compounds produced by the process of this invention may be described by formula as follows:

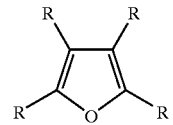

wherein each R is independently selected from the group consisting of hydrogen and alkyl radicals having from 1 to 6 carbon atoms, the total carbon atoms in the R radicals being in the range of 0 to 6.

The advantageous technical effects of this invention are demonstrated by a series of examples, as described below. The embodiments of the invention on which the examples are based are illustrative only, and do not limit the scope of the invention. The significance of the examples is better understood by comparing these embodiments of the invention with certain controlled evaluations, which do not possess the distinguishing features of this invention.

Materials and Methods

Pulse Reactor Evaluations

The evaluations of Examples 1–4 and Control E were performed using a pulse reactor in which butadiene was oxidized.

A stream of helium is passed through three sample injection valves, then through a reactor heated by a tube furnace, then through a thermal conductivity detector followed by another 6 way gas sampling valve. Two 4 way valves are situated before and after the reactor to allow the reactor to be bypassed for calibration purposes.

The 6 way gas sampling valves are configured to inject pulses of water, oxygen, and butadiene into the helium stream. They are housed in an oven kept at 170° C. The first valve is fed by an ISCO pump containing water which vaporizes in the oven, the second is connected to a 20% $O_2$ in He cylinder, and the third is fed from a butadiene cylinder. The size of the pulse is determined by the loop size on the valves, which are 0.5 ml for steam and 0.05 ml for $O_2$/He and butadiene. In Table 2, Example 1 is evaluated in the pulse reactor using the following sequence: 8 pulses of air, 1 pulse of butadiene/water mixture, then 8 pulses of air in order to reoxidize the catalysts. The selectivity and conversions are measured from the butadiene/water pulse, and hence, the oxidation is accomplished using the lattice oxygen in the catalyst. In Table 2, Example 1A, the pulses consist of a butadiene/water/air mixture derived from simultaneously admitting the 0.5 ml pulse for steam, 0.05 ml pulse for O2/He and 0.05 ml pulse for butadiene. Conversion and selectivity are calculated by averaging data derived from three of the consecutive butadiene/water/air pulse combinations.

After the pulse(s) is injected into the helium stream, it passes either through or around the reactor and then through one side of a thermal conductivity detector, through a sample loop and then through the other side of the detector. The pulse is injected into a gas chromatograph ("GC")/mass spectroscopy ("MS") analyzer when it is in the sample loop. Passing the sample through both sides of the thermal conductivity detector before and after the sample loop allows determination of whether the pulse is completely captured. The sample valve injects the sample onto a capillary GC column.

The percent conversion to, and percent selectivity to, furan was calculated for each evaluation, and the results are reported in Table 2. Butadiene conversion data are obtained by comparing the area of the butadiene GC peak in the reaction product with that in the feed. The feed is determined by using the reactor bypass. Relative response factors for butane, CO and $CO_2$ are determined from a standard cylinder. Furan and maleic anhydride are dissolved in tetrahydrofuran ("THF") to obtain the relative response factor. Selectivity to furan is determined by calculating the moles product/moles butadiene reacted=moles product/(moles butadiene final−moles butadiene initial).

Fixed Bed Reactor Evaluations

The evaluations of Examples 1 and 5 and Controls A–D are performed using a fixed bed reactor in which butadiene is oxidized.

The catalyst testing facility consists of six micro-reactors which are connected to a common feed source and a common GC. Each of the micro-reactors consists of a 5.0 cm by 0.64 cm stainless steel tube which is immersed in an individual sandbath to maintain isothermal conditions. The feed composition and individual reactor flow rates are metered by commercially available mass flow controllers (Tylan Model FC-260, available from Tylan Corp., Torrance, Calif.). The feeds by are 8.64 mole % butadiene, 10 mole % air, 0.45 mole % $N_2$ and the balance helium, with no water. All exit gas lines are heated to 200° C. and connected to a multiport Valco valve for the on-line analysis of products using a commercially available GC (Hewlett-Packard 5890 Series II, Hewlitt-Packard, Palo Alto, Calif.). A computer program controls the Valco valve to select a reactor or feed stream to fill the 0.5 ml sample loop for injection in the GC. The GC is used to analyze for butane, maleic anhydride, acetic acid, acrylic acid, other $C_1$ to $C_4$ hydrocarbons, oxygen, carbon monoxide, carbon dioxide, nitrogen and water.

The percent conversion to, and percent selectivity to, furan is calculated for each evaluation, and the results are reported in Table 1. Butadiene conversion data are obtained by comparing the area of the butadiene GC peak in the reaction product with that in the feed. Selectivity to furan is determined by calculating the moles of product and dividing by the moles butadiene reacted.

The particular catalysts used in Examples 1–5 and Controls A–E are prepared, and are identified, as described below.

Control A

3.0 g of $MoO_3$ (Alfa Aesar Chemicals #11837, Ward Hill, Mass.) is contacted with 8.3 ml of an aqueous, 1 M solution of $Cu(NO_3)_2$ (Alfa Chemicals #12523, Ward Hill, Mass.). The slurry is agitated at room temperature under a blanket of nitrogen. Following a slow evaporative procedure at room temperature, the material is calcined at 250° C. for 1 hour and 500° C. for five hours to produce the powder. The material is subsequently pressed into disks and screened through −40/+60 mesh screens to produce the granulated powder, which is used for microreactor evaluations. Elemental compositional analysis by ICP (inductively coupled plasma) analysis of the final material is: Cu, 12.286 wt %; Mo, 55.5304 wt %.

Control B

3.0 g of MgO (EM Science #MX00658-2, Cincinnati, Ohio) is contacted with 29.6 ml, 1 M aqueous solution of $Cu(NO_3)_2$. Each slurry is agitated at room temperature under a blanket of nitrogen. Following a slow evaporative procedure at room temperature, the material is calcined at 250° C. in air for 1 hour and 500° C. for five hours to produce the powder. The material is subsequently pressed into disks and screened through-40/+60 mesh screens to produce the granulated powder, which is used for microreactor evaluations. The elemental composition analysis of the final material is: Cu, 33.1506 wt %; Mg, 0.142 wt %.

Control C

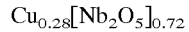

3.0 g of $Nb_2O_5$ (Alfa Aesar Chemicals #51125, Ward Hill, Mass.) is contacted with 8.8 ml of 0.5 M aqueous solution of $Cu(NO_3)_2$ (Fischer Scientific, Pittsburgh, Pa.). Each slurry is agitated at room temperature under a blanket of nitrogen. Following a slow evaporative procedure at room temperature, the material is calcined at 250° C. in air for 1 hour and 500° C. for five hours to produce the powder. The material is subsequently pressed into disks and screened through −40/+60 mesh screens to produce the granulated powder, which is used for microreactor evaluations. The elemental composition analysis by ICP of the final material is: Cu, 9.4170 wt %; Nb, 60.1115 wt %.

Control D $$Cu_{0.28}[Bi_2O_3]_{0.72}$$

3.0 g of $Bi_2O_3$ (J. T. Baker and Co. #1158-01, Phillipsburg, N.J.) is contacted with 5.0 ml of 0.5 M of aqueous $Cu(NO_3)_2$ solution (Fischer Scientific, Pittsburgh, Pa.). Each slurry is agitated at room temperature under a blanket of nitrogen. Following a slow evaporative procedure at room temperature, the material is calcined at 250° C. in air for 1 hour and 500° C. for five hours to produce the powder. The material is subsequently pressed into disks and screened through −40/+60 mesh screens to produce the granulated powder, which is used for microreactor evaluations. The elemental composition analysis by ICP of the final powder is: Cu, 4.3504 wt %; Bi, 12.5590 wt %.

Control E $$Bi_{1.95}Pb_{0.05}MoO_{5.95}$$

35.32 g of $(NH_4)_6Mo_7O_{24} \cdot 4H_2O$ (Alfa Aesar Chemicals #F26H32, Ward Hill, Mass.), 189.2 g of $Bi(NO_3)_3 \cdot 5H_2O$ (Aldrich Chemicals, Milwaukee, Wis., lot 004120), 3.32 g of $Pb(NO_3)_2$ (Aldrich Chemicals, Milwaukee, Wis., lot #13717TQ) and three liters of water are loaded into a five liter round bottom flask equipped with a mechanical stirrer, reflux condenser, and mechanical stirrer. The materials are refluxed under nitrogen for 24 hours, and subsequently filtered through a fine glass frit funnel to remove unreacted nitrates. The solid residue is loaded into the five liter round bottom flask and refluxed for an additional twenty-four hours. The procedure is repeated for four times, and the final product is dried in a vacuum oven ft 120° C. for twenty-four hours. Powder X-ray diffraction analysis indicates a koechlinite type phase for the final material, with a surface area of 3–5 m²/g. For reactor evaluations, material is calcined at 250° C. in air for 1 hour and 500° C. for five hours to produce the powder. The material is subsequently pressed into disks and screened through −40, +60 mesh screens to produce the granulated powder, which was used for microreactor evaluations. The elemental composition analysis by ICP of the resulting powder indicates Bi 70.0 wt %; Pb 0.27 wt %; Mo 16.0 wt %.

EXAMPLES 1 and 1A $$Cu_{0.29}[Bi_{1.95}Pb_{0.05}MoO_{5.95}]_{0.72}O_x$$

3.0 g of the solid derived from Control E, the precursor to $Bi_{1.95}Pb_{0.05}MoO_{5.95}$ which has not been calcined (Control E without the calcination protocol) is contacted with 3.94 ml of 0.5 M copper nitrate solution ($Cu(NO_3)_2$, Fischer Scientific #725840). Each slurry is agitated at room temperature under a blanket of nitrogen. Following a slow evaporative procedure at room temperature, the material is calcined at 250° C. for 1 hour and 500° C. for five hours to produce the powder. The material is subsequently pressed into disks and screened through −40/+60 mesh screens to produce the granulated powder, which is used for microreactor evaluations.

EXAMPLE 2

$$Cu_{0.10}[Bi_{1.95}Pb_{0.05}MoO_{5.95}]_{0.5}O_x$$

3.0 g of the solid derived from Control E which has not been calcined (Control E without the calcination protocol) is contacted with 10.0 ml of 0.005 M $Cu(NO_3)_2$ (Fisher Scientific, #725840). Each slurry is agitated at room temperature under a blanket of nitrogen. Following a slow evaporative procedure at room temperature, the material is calcined at 250° C. for 1 hour, and 500° C. for five hours, to produce the powder. The material is subsequently pressed into disks and screened through −40/+60 mesh screens to produce the granulated powder, which is used for microreactor evaluations. The elemental composition (by ICP analysis) of the final powder is: Cu, 0.1065 wt %; Pb, 0.5527 wt %; Bi, 57.7395 wt %; Mo, 15.5395 wt %.

EXAMPLE 3

$$Au_{0.29}[Bi_{1.95}Pb_{0.05}MoO_{5.975}]_{0.71}O_x$$

The identical procedure described in Example 1 is employed, except that 7.824 ml of 0.2518 M aqueous solution of $AuCl_3$ (Aldrich, 10425PS) is used instead of the copper nitrate solution.

EXAMPLE 4

$$V_{0.29}[Bi_{1.95}Pb_{0.05}MoO_{5.975}]_{0.5}O_x$$

The identical procedure described in Example 1 is employed, except that 25.772 ml of 0.0764 M aqeuous solution of $NH_4VO_3$ (Alfa Aesoar, #115F36) is used instead of the copper nitrate solution.

EXAMPLE 5

$$V_{0.5}[Bi_{1.95}Pb_{0.05}MoO_{5.95}]_{0.5}O_x$$

3.0 g of the solid derived from Control E which has not been calcined (Control E without the calcination protocol) is contacted with 64.43 ml of 0.07644M $NH_4VO_3$ (Alfa Aesar, #115F36). Each slurry is agitated at room temperature under a blanket of nitrogen. Following a slow evaporative procedure at room temperature, the material is calcined at 250° C. for 1 hour, and 500° C. for five hours, to produce the powder. The material is subsequently pressed into disks and screened through −40/+60 mesh screens to produce the granulated powder, which is used for microreactor evaluations.

The catalysts used in the exemplary and controlled evaluations are pelletized at 1.38×10⁶ kPa into disks and subsequently crushed and sieved through −40/+60 mesh screens. Approximately 0.9 cc of catalyst are used for each evaluation. The weight of each catalyst used is adjusted based on solids bulk density to yield the same contact time (0.75 seconds) for each evaluation (i.e., equal packed bed volumes are employed). The results of oxidizing butadiene in the fixed bed microreactor, as described above, and in the pulse reactor, as described above, using the catalysts as designated above for Examples 1-5 and Controls A–E are shown in Table 1 and Table 2 below. These examples illustrate the lattice oxygen effect.

TABLE 1

Reactor Data: Fixed Bed Microreactor System

| | Catalyst Composition | Temp. °C. | % conversion | % selectivity to furan (relative to $C_4H_6$) |
|---|---|---|---|---|
| Example 1 | $Cu_{0.29}[Bi_{1.95}Pb_{0.05}MoO_{5.95}]_{0.72}O_x$ | 400 | 37.9 | 11.4 |
| Control A | $Cu_{0.28}[MoO_3]_{0.72}$ | 394 | 29.7 | 10.8 |
| Control B | $Cu_{0.28}[MgO]_{0.72}$ | 415 | 21.5 | 0.2 |
| Control C | $Cu_{0.28}[Nb_2O_5]_{0.72}$ | 416 | 22.6 | 1.9 |
| Control D | $Cu_{0.28}[Bi_2O_3]_{0.72}$ | 398 | 7.8 | 1.2 |
| Example 5 | $V_{0.5}[Bi_{1.95}Pb_{0.05}MoO_{5.95}]_{0.5}O_x$ | 398 | 18.2 | 14.6 |

TABLE 2

Reactor Data: Pulse Reactor

| | Catalyst Composition | Temp. °C. | % conversion | % selectivity to furan (relative to $C_4H_6$) |
|---|---|---|---|---|
| Example 1 | $Cu_{0.29}[Bi_{1.95}Pb_{0.05}MoO_{5.95}]O_x$ | 320 | 12 | 68 (butadiene with water) |
| Example 1A | | 320 | 14 | 61 (butadiene with water and air) |
| Example 2 | $Cu_{0.10}[Bi_{1.95}Pb_{0.05}MoO_{5.95}]_{0.5}O_x$ | 259 | 32 | 53 |
| | | 307 | 59 | 50 |
| Control E | $Bi_{1.95}Pb_{0.05}MoO_{5.95}$ | 320 | 24 | 3 |
| Example 3 | $Au_{0.29}[Bi_{1.95}Pb_{0.05}MoO_{5.975}]_{0.71}O_x$ | 320 | 28 | 13 |
| Example 4 | $V_{0.29}[Bi_{1.95}Pb_{0.05}MoO_{5.975}]_{0.71}O_x$ | 320 | 19 | 13 |

It may be seen from the data in Tables 1 and 2 that, when butadiene is oxidized in the presence of a catalyst of this invention, as in Examples 1–5, a more desirable balance of high percent conversion and high percent selectivity to furan is obtained as compared to the results of an oxidation conducted in the presence of any of the catalysts of Controls A–E.

What is claimed is:

1. A process for the oxidation of an alkene or alkadiene, having 4–10 carbon atoms, to the corresponding furan compound in an oxygen-containing environment; comprising
   (a) contacting the alkene or alkadiene with a catalyst consisting essentially of bismuth, lead, molybdenum, oxygen, and at least one metal selected from the group consisting of copper, gold and vanadium, under suitable vapor-phase reaction conditions for the conversion of the alkene or alkadiene to the corresponding furan compound; and
   (b) recovering at least a portion of the furan compound.

2. A process according to claim 1 wherein the catalyst is a compound of the formula $Q_d[Bi_aPb_bMo_cO_y]_eO_x$ wherein
   Q is selected from the group consisting of copper, gold and vanadium, and mixtures thereof;
   a is about 1 to about 3;
   b is about 0.01 to about 0.1;
   c is about 0.1 to about 2;
   d is about 0.01 to about 2;
   e is about 0.01 to about 2; and
   y and x are independently numbers sufficient so that the oxygen present balances the charges of the other elements in the compound.

3. A process according to claim 2 wherein a is about 1.5 to about 2.0; b is about 0.025 to about 0.075; c is about 0.5 to about 1.5, d is about 0.05 to about 1; and e is about 0.5 to about 1.

4. A process according to claim 2 wherein a is about 1.95; b is about 0.05; c is 1; and d is about 0.029 to about 0.5.

5. A process according to claim 2 wherein Q is copper.
6. A process according to claim 2 wherein Q is gold.
7. A process according to claim 2 wherein Q is vanadium.
8. A process according to claim 1 wherein the oxygen in the oxygen-containing environment is provided by an external feed.
9. A process according to claim 1 wherein the oxygen in the oxygen-containing environment is provided solely by the oxygen contained in the catalyst.
10. A process according to claim 1 further comprising a step of selecting 1,3-butadiene as the alkadiene.
11. A process according to claim 9 further comprising a step of selecting 1,3-butadiene as the alkadiene.
12. A process for the oxidation of an alkene or alkadiene, having 4–10 carbon atoms, to the corresponding furan compound in an oxygen-containing environment; comprising
   (a) contacting the alkene or alkadiene with a catalyst comprising a compound of the formula $Q_d[Bi_aPb_bMo_cO_y]_eO_x$ wherein
      Q is selected from the group consisting of copper, gold and vanadium, and mixtures thereof;
      a is about 1 to about 3;
      b is about 0.01 to about 0.1;
      c is about 0.1 to about 2;
      d is about 0.01 to about 2;
      e is about 0.01 to about 2; and
      y and x are independently numbers sufficient so that the oxygen present balances the charges of the other elements in the compound under suitable vapor-phase reaction conditions for the conversion of the alkene or alkadiene to the corresponding furan a compound; and
   (b) recovering at least a portion of the furan compound.

13. A process according to claim 12 wherein a is about 1.5 to about 2.0; b is about 0.025 to about 0.075; c is about 0.5 to about 1.5, d is about 0.05 to about 1; and e is about 0.5 to about 1.

14. A process according to claim 12 wherein a is about 1.95; b is about 0.05; c is 1; and d is about 0.029 to about 0.5.

15. A process according to claim 12 wherein Q is copper.

16. A process according to claim 12 wherein Q is gold.

17. A process according to claim 12 wherein Q is vanadium.

18. A process according to claim 12 wherein the oxygen in the oxygen-containing environment is provided by an external feed.

19. A process according to claim 12 wherein the oxygen in the oxygen-containing environment is provided solely by the oxygen contained in the catalyst.

20. A process according to claim 12 further comprising a step of selecting 1,3-butadiene as the alkadiene.

21. A process according to claim 19 further comprising a step of selecting 1,3-butadiene as the alkadiene.

22. A mixed metal oxide catalyst consisting essentially of bismuth, lead, molybdenum and oxygen, and at least one metal selected from the group consisting of copper, gold and vanadium.

23. A catalyst according to claim 22 which is a compound of the formula $Q_d[Bi_aPb_bMo_cO_y]_eO_x$ wherein Q is selected from the group consisting of copper, gold and vanadium, and mixtures thereof;

a is about 1 to about 3;

b is about 0.01 to about 0.1;

c is about 0.1 to about 2;

d is about 0.01 to about 2;

e is about 0.01 to about 2; and y and x are independently numbers sufficient so that the oxygen present balances the charges of the other elements in the compound.

24. A catalyst according to claim 23 wherein a is about 1.5 to about 2.0; b is about 0.025 to about 0.075; c is about 0.5 to about 1.5; d is about 0.05 to about 1; and e is about 0.5 to about 1.

25. A catalyst according to claim 23 wherein a is about 1.95; b is about 0.05; c is 1; and d is about 0.029 to about 0.5.

26. A catalyst according to claim 23 wherein Q is copper.

27. A catalyst according to claim 23 wherein Q is gold.

28. A catalyst according to claim 23 wherein Q is vanadium.

29. A mixed metal oxide catalyst comprising a compound of the formula $Q_d[Bi_aPb_bMo_cO_y]_eO_x$ wherein Q is selected from the group consisting of copper, gold and vanadium, and mixtures thereof;

a is about 1 to about 3;

b is about 0.01 to about 0.1;

c is about 0.1 to about 2;

d is about 0.01 to about 2;

e is about 0.01 to about 2; and y and x are independently numbers sufficient so that the oxygen present balances the charges of the other elements in the compound.

30. A catalyst according to claim 29 wherein a is about 1.5 to about 2.0; b is about 0.025 to about 0.075; c is about 0.5 to about 1.5; d is about 0.05 to about 1; and e is about 0.5 to about 1.

31. Catalyst according to claim 29 wherein a is about 1.95; b is about 0.05; c is 1; and d is about 0.029 to about 0.5.

32. A catalyst according to claim 29 wherein Q is copper.

33. A catalyst according to claim 29 wherein Q is gold.

34. A catalyst according to claim 29 wherein Q is vanadium.

* * * * *